United States Patent [19]

Kikugawa et al.

[11] Patent Number: 4,603,210
[45] Date of Patent: Jul. 29, 1986

[54] PREPARATION PROCESS OF ACEMETACIN

[75] Inventors: Yasuo Kikugawa, Sakado; Yoshinori Kyotani, Higashi-yamato, both of Japan

[73] Assignees: Troponwerke GmbH & Co. KG., Cologne, Fed. Rep. of Germany; Kowa Company, Aichi, Japan

[21] Appl. No.: 599,096

[22] Filed: Apr. 11, 1984

[30] Foreign Application Priority Data

Apr. 28, 1983 [JP] Japan ................... 58-75869

[51] Int. Cl.$^4$ ........................... C07D 209/28
[52] U.S. Cl. ................................. 548/501
[58] Field of Search ........................ 548/501

[56] References Cited

U.S. PATENT DOCUMENTS

| 3,483,220 | 12/1969 | Gaines et al. | 548/501 |
| 4,104,278 | 8/1978 | Boltze et al. | 548/501 |
| 4,165,428 | 8/1979 | Noda et al. | 548/501 |
| 4,181,740 | 1/1980 | Zumin et al. | 548/501 |

FOREIGN PATENT DOCUMENTS

| 837084 | 3/1970 | Canada | 548/501 |
| 1551429 | 12/1968 | France | 548/501 |
| 1176348 | 1/1970 | United Kingdom | 548/501 |

OTHER PUBLICATIONS

Boltze, Drug Res., 30 (II), pp. 1314 et seq. (1980).

Primary Examiner—Glennon H. Hollrah
Assistant Examiner—D. B. Springer
Attorney, Agent, or Firm—Sprung, Horn, Kramer & Woods

[57] ABSTRACT

A process for preparing acemetacin which process comprises removing a protecting group, which is other than tetrahydropyranyl group and is removable under acidic conditions, from an acemetacin ester represented by the formula

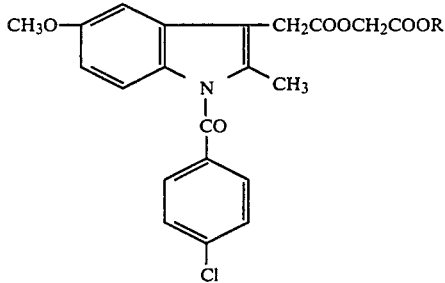

wherein R means the protecting group, under the acidic conditions.

5 Claims, No Drawings

PREPARATION PROCESS OF ACEMETACIN

This invention relates to a novel preparation process of [1-(p-chlorobenzoyl)-5-methoxy-2-methyl-3-indolylacetoxy acetic acid] (hereinafter called "acemetacin") which is useful as an anti-inflammatory agent and is represented by the following formula (I):

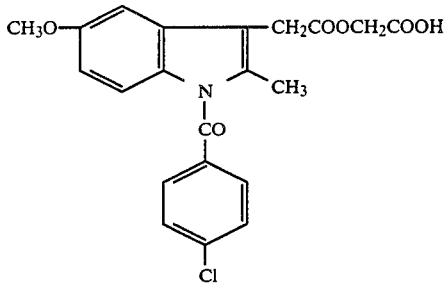

The preparation of acemetacin from, as a raw material, 1-(p-chlorobenzoyl)-5-methoxy-2-methyl-3-indolylacetic acid (hereinafter called "indomethacin") represented by the formula (II) has conventionally been carried out by reacting benzyl bromoacetic acid with an alkali metal salt of indometacin to form the benzyl ester of acemetacin and then subjecting the benzyl ester to catalytic reduction so as to remove the benzyl group.

It was, however, difficult to isolate and purify acemetacin, which had been prepared in accordance with the above process, by the recrystallization technique, because the inclusion of indomethacin (II), an unreacted raw material, in the thus-obtained acemetacin was unavoidable and the solubility of acemetacin in each recrystallization solvent is higher than that of indomethacin.

In the meantime, the present inventors made a variety of investigation toward developing preparation processes of acemetacin which processes are free of such a drawback. As a result, the present inventors found a process which proceeds by way of the phenycyl ester of acemetacin, on which process a patent application has already been filed (see, Japanese Patent Laid-open No. 192361/1982). The present inventors have conducted a further research. As a result, it has been found that use of a compound of the below-described formula (III), which is extremely inexpensive, as a raw material permits to undergo a reaction with indomethacin (II) under mild conditions and hence to provide an acemetacin ester of the below-described formula (IV) with high yield as well as the protecting group R is solely and specifically removed without giving an influence to the other functional groups so as to obtain acemetacin of high purity with high yield when the acemetacin ester (IV) is treated with an acid, leading to completion of this invention.

Namely, this invention provides a process for obtaining acemetacin (I) by reacting a compound represented by the general formula (III):

X—CH₂COO—R   (III)

wherein X means a halogen atom and R denotes a protecting group other than tetrahydropyranyl group and removable under acidic conditions with indomethacin (II) to form an acemetacin ester represented by the general formula (IV):

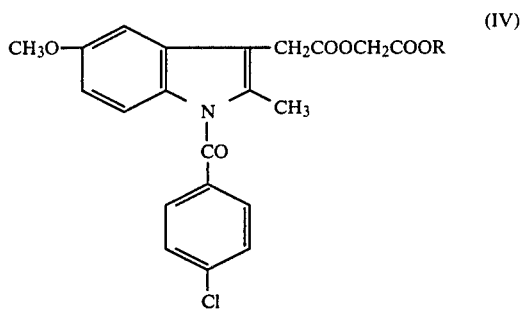

wherein R has the same meaning as defined above, and then removing the protecting group under the acidic conditions.

As protecting groups represented by R in the general formula (III), any groups may be employed so long as they can be removed when treated with an acid such as trifluoroacetic acid, trichloroacetic acid, hydrogen fluoride, formic acid, hydrochloric acid/dioxane or the like. As exemplary protecting groups may be mentioned t-butyl group, p-methoxy-benzyl group, triphenylmethyl group, diphenylmethyl group etc. On the other hand, chlorine, iodine, fluorine or bromine may be used as X in the formula (III). The compound of the formula (III), for example, t-butyl chloroacetate may be readily prepared by reacting monochloroacetic acid with isobutylene in the presence of an acid (Chemical Abstracts, 56, 5968).

In the practice of the process of this invention, indomethacin (II) and the compound of the formula (III) are first of all reacted with each other in a solvent and in the presence of potassium fluoride, cesium fluoride or the like to prepare the acemetacin ester (IV). Acetonitrile, dimethylsulfoxide, tetrahydrofuran or the like may preferably be used as the solvent. It may be preferred to conduct the reaction at a temperature of from room temperature to 150° C. and for a time period of from 30 minutes to several hours. Incidentally, the acemetacin ester (IV) may be obtained with high purity when an alkali metal salt of an organic acid such as sodium formate, potassium acetate, sodium propionate or the like is added in the reaction. Acemetacin (I) is next be obtained by treating the thus-obtained acemetacin ester (IV) with the above-mentioned acid. It is preferable to carry out the reaction at room temperature or with cooling for 1 to several hours. This reaction may be allowed to proceed with good yield by an addition of anisole, indole, 2-methylindole, dithiothreitol, 3-mercaptoethanol or the like.

As mentioned above, the present invention provides an industrially advantageous process which permits to prepare acemetacin (I) by simple procedures under mild conditions.

The invention will hereinafter be described by the following Examples.

EXAMPLE 1

Dissolved in 80 ml of dimethylformamide were 8.0 g of indomethacin, 7.3 g of potassium fluoride and 4.6 g of t-butyl chloroacetate. The resulting solution was stirred at 120°–130° C. for 1 hour. After cooling, the liquid reaction mixture was poured into 400 ml of a 10% solution of sodium carbonate in water. The resulting crystalline deposit was collected by filtration, washed with water, and then dried mixture was poured into 400 ml of a 10% solution of sodium carbonate in water. The resulting crystalline deposit was collected by filtration, washed with water, and then dried to give yellowish crystals. The crystals were thereafter recrystallized from benzene-n-hexane to obtain 9.60 g of the t-butyl ester of acemetacin, which had a melting point of 101°–101.5° C., as pale yellowish crystals (yield: 90.9%).

EXAMPLE 2

One hundred grams of indomethacin, 91.25 g of potassium fluoride and 13.5 g of sodium propionate were suspended in 500 ml of dimethylformamide, followed by an addition of 64.31 g of t-butyl chloroacetate. The resultant mixture was stirred and then stirred for 1 hour in a water bath of 90° C. After cooling, the mixture was poured into 5 liters of a 10% solution of sodium carbonate in water, followed by an addition of water to make the total volume be 20 liters. The resulting yellowish solid deposit was separated and then taken up in 1.65 liters of benzene. The thus-prepared solution was washed with water and, after drying, the solvent was driven off. The residue was recrystallized from n-hexane, thereby obtaining 126.1 g of the t-butyl ester of acemetacin as pale yellowish crystals (yield: 95.6%)

EXAMPLE 3

The t-butyl ester of acemetacin was obtained (yield: 79.5%) following the procedures of Example 1 except that cesium fluoride and t-butyl bromoacetate were used respectively in place of potassium fluoride and t-butyl chloroacetate.

EXAMPLE 4

Dissolved in a mixture of 50 ml of trifluoroacetic acid and 1 ml of anisole was 2.69 g of the t-butyl ester of acemetacin. The resultant solution was stirred for 1 hour at low temperatures. Trifluoroacetic acid was then caused to evaporate under reduced pressure. The residue was successively added with ethyl acetate and n-hexane. The thus-prepared mixture was then allowed to stand, thereby obtaining 2.26 g of acemetacin having a melting point of 142°–146° C. (yield: 95.4%). It was recrystallized from acetone-n-hexane to obtain asemetacin having a melting point of 146°–148° C. It did not show any melting point depression when subjected to a mixed examination with its standard product. Its IR, MS and NMR data were all in conformity with those of the standard product.

EXAMPLE 5

The t-butyl ester of acemetacin (201 mg) was dissolved in 3.5 ml of formic acid and the resultant solution was stirred at room temperature for 3 hours. Formic acid was caused to evaporate under reduced pressure. The residue was taken up in 400 ml of a 1:5 liquid mixture of acetone and benzene and insoluble material was removed by filtration. The solvent was then driven off from the filtrate. The residue was recrystallized from benzene to obtain 172 mg of acemetacin as pale yellowish crystals (yield: 97.1%).

We claim:

1. A process for preparing acemetacin represented by the following formula (I):

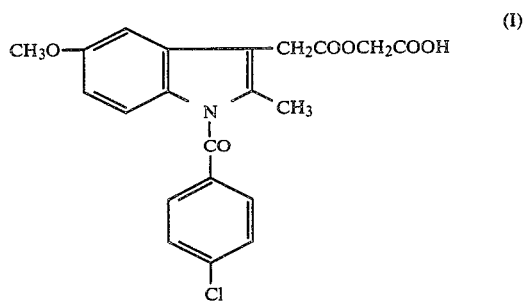

which process comprises reacting a compound represented by the following general formula (III):

$$X-CH_2COO-R \quad (III)$$

wherein X means a halogen atom and R denotes a t-butyl group with 1-(p-chlorobenzoyl)-5-methoxy-2-methyl-3-indolylacetic acid represented by the following formula (II):

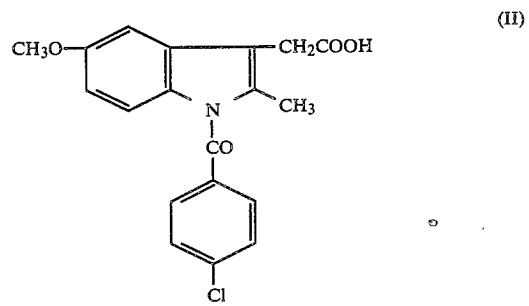

at a temperature of from room temperature to 150° C. at a time period of 30 minutes to several hours to form an acemetacin ester represented by the following formula (IV):

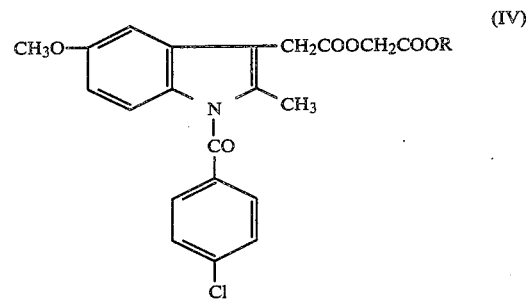

wherein R has the same meaning as defined above, and then removing the protecting group from the acemetacin ester by treating it at room temperature or under cooling for 1 to several hours with trifluoro acetic acid, trichloroacetic acid, hydrogen fluoride, formic acid, hydrochloric acid/acetic acid, hydrobromic and/acetic acid or hydrochloric acid/dioxane.

2. The process of claim 1 wherein X is chlorine, iodine, fluorine or bromine.

3. The process of claim 1 wherein the reaction of 1-(p-chlorobenzoyl)-5-methoxy-2-methyl-3-indolylacetic (II) and compound of general formula (III) is carried out in acetonitrile, dimethylsulfoxide or tetrahydrofuran in the presence of potassium fluoride or cesium fluoride.

4. The process of claim 3 wherein the reaction is carried out in the presence of sodium formate, potassium acetate or sodium propionate.

5. The process of claim 1 wherein the reaction is carried out in the presence of anisolve, indole, 2-methylindole, dithiothreitol or 3-mercaptoethanol.

* * * * *